United States Patent
Shintake

(10) Patent No.: US 9,576,770 B2
(45) Date of Patent: Feb. 21, 2017

(54) LEED FOR SEM

(71) Applicant: Okinawa Institute of Science and Technology School Corporation, Okinawa (JP)

(72) Inventor: Tsumoru Shintake, Okinawa (JP)

(73) Assignee: OKINAWA INSTITUTE OF SCIENCE AND TECHNOLOGY SCHOOL CORPORATION, Okinawa (JP)

( * ) Notice: Subject to any disclaimer, the term of this patent is extended or adjusted under 35 U.S.C. 154(b) by 0 days.

(21) Appl. No.: 14/888,414

(22) PCT Filed: May 14, 2014

(86) PCT No.: PCT/JP2014/002556
§ 371 (c)(1),
(2) Date: Oct. 30, 2015

(87) PCT Pub. No.: WO2014/185074
PCT Pub. Date: Nov. 20, 2014

(65) Prior Publication Data
US 2016/0071690 A1    Mar. 10, 2016

Related U.S. Application Data

(60) Provisional application No. 61/823,507, filed on May 15, 2013.

(51) Int. Cl.
*G21K 5/04* (2006.01)
*H01J 37/244* (2006.01)
*H01J 37/295* (2006.01)

(52) U.S. Cl.
CPC ........ *H01J 37/244* (2013.01); *H01J 37/2955* (2013.01); *H01J 2237/24578* (2013.01)

(58) Field of Classification Search
USPC .... 250/305, 306, 307, 309, 310, 311, 396 R, 250/397, 492.1, 492.3
See application file for complete search history.

(56) References Cited

U.S. PATENT DOCUMENTS 4,978,855 A    12/1990  Liebl et al.
5,266,809 A    11/1993  Engel
(Continued)

FOREIGN PATENT DOCUMENTS

CN    101647085 A    2/2010
JP    H02-216748 A    8/1990
(Continued)

OTHER PUBLICATIONS

Zangwill, "Physics at Surfaces", Cambridge University Press (1988), p. 33.
(Continued)

*Primary Examiner* — Nicole Ippolito
(74) *Attorney, Agent, or Firm* — Chen Yoshimura LLP

(57) ABSTRACT

A low energy electron diffraction (LEED) detection module (100) includes: a first vacuum chamber for receiving diffracted electrons from a specimen (109); a larger second vacuum chamber connected to the first vacuum chamber to receive the diffracted electrons that have been transported through the first vacuum chamber; a two-dimensional electron detector disposed in the second vacuum chamber to detect the diffracted electrons; a potential shield (106) disposed generally along an inner surface of the first vacuum chamber and an inner surface of the second vacuum chamber; a magnetic lens (105) to expand a beam of the diffracted electrons that have been transported through the first vacuum chamber towards the two-dimensional electron detector; and a generally plane-shaped energy filter (103) to
(Continued)

repel electrons having an energy lower than the probe beam (203) of electrons that impinges on the specimen (109).

12 Claims, 3 Drawing Sheets

(56) References Cited

U.S. PATENT DOCUMENTS

| | | | |
|---|---|---|---|
| 5,675,148 | A | 10/1997 | Marui |
| 5,969,356 | A | 10/1999 | Grzelakowski |
| 6,198,095 | B1 | 3/2001 | Staib |
| 6,492,644 | B1 | 12/2002 | Staib |
| 7,348,566 | B2 | 3/2008 | Tromp |
| 7,902,502 | B2 | 3/2011 | David |
| 9,123,501 | B2 * | 9/2015 | Fukuda ............. H01J 37/153 |
| 2009/0189072 | A1 * | 7/2009 | Egan ................. H01J 49/40 250/287 |
| 2010/0187433 | A1 | 7/2010 | Eastham |
| 2011/0049344 | A1 | 3/2011 | Dobashi et al. |

FOREIGN PATENT DOCUMENTS

| | | |
|---|---|---|
| JP | 10-208682 A | 8/1998 |
| JP | 2000-215842 A | 8/2000 |
| JP | 2001-35434 A | 2/2001 |
| JP | 2002-131249 A | 5/2002 |
| JP | 2010-517233 A | 5/2010 |

OTHER PUBLICATIONS

International Search Report (ISR) issued in PCT/JP2014/002556 mailed in Jun. 2014.

Written Opinion (PCT/ISA/237) issued in PCT/JP2014/002556 mailed in Jun. 2014.

Frömter et al., "A miniaturized detector for high-resolution SEMPA", Appl. Phys. A 76, pp. 869-871 (2003).

Wiessner et al., "Design considerations and performance of a combined scanning tunneling and scanning electron microscope", Rev. Sci. Instrum., Oct. 1997, vol. 68, No. 10, pp. 3790-3798.

Ichinokawa et al., "Low Energy Scanning Electron Microscopy Combined With Low Energy Electron Diffraction", Surface Science 176 (1986), p. 397-414.

Anders et al., "Photoemission electron microscope for the study of magnetic materials", Review of Scientific Instruments, October 1999, vol. 70, No. 10, p. 3973-3981.

Oepen et al., "Imaging of Magnetic Microstructures at Surfaces", Journal De Physique, Dec. 1988, Symposium C8, Supplement to No. 12 , vol. 49, p. 1853-1857.

Shintake, "LEED for SEM", Apr. 2013, p. 1-5.

Chinese Office Action dated Jul. 11, 2016, in a counterpart Chinese patent application No. 201480028221.8.

European Search Report dated Dec. 20, 2016, in a counterpart European patent application No. 14797934.8.

\* cited by examiner

LEED FOR SEM

TECHNICAL FIELD

The present invention relates to a LEED (Low Energy Electron Diffraction) device, and in particular, to a LEED (Low Energy Electron Diffraction) detection module.

BACKGROUND ART

LEED has been widely used to analyze surface structure (crystalline) of solid material by the electron diffraction, i.e., Bragg's diffraction of de Broglie wave of low energy electron. LEED is very sensitive to the atomic arrangement near surface; it provides information of dislocations, impurities and contaminations of solid material. LEED is inevitable device in surface science. See Non Patent Literature No. 1.

However, as shown in Non Patent Literature No. 1, conventional LEED apparatus uses electron energy filters made by spherical shaped metal grids in its detection components, usually 5 cm to 10 cm in diameter. Therefore, the size of the LEED apparatus is large, and the it does not fit to typical equipment ports of commercial SEMs (Scanning Electron Microscopes).

In more detail, in the conventional LEED, thermionic electron gun is used to generate a probe electron beam (typically, 0.1 mm diameter, 1 micro-ampere or less, a few 100 Volts) impinging on a sample surface from the normal direction. The inelastic back-scattered electrons are rejected through energy filtering grids made by spherical shaped metal screens (usually 5 cm to 10 cm in diameter). The elastic back-scattered electrons (diffraction) are detected by phosphor screen and a CCD camera. Because it uses fairly large grids, the conventional LEED does not fit within SEM chambers. Also, because the grids are spherical shape, it is not easy to make finer meshes. When the LEED unit is large, it may interfere with other detectors, such as, STEM detector or XRD detector.

Furthermore, even through Bragg's diffraction is caused by atomic arrangement around sample surface, the conventional LEED does not work for imaging the atomic structure; it just shows averaged Bragg's diffraction from crystalline structure. Reason is that the spot size of the probe electron beam in typical LEED apparatus is around 100 micrometers, which is too large, and finest interference fringes associated between two points at both edges on the spot will exceeds the finest pitch of CCD or CMOS detector, and will be hidden in the diffraction image. As a result, it is not possible to recover the real image using holography or iterative phase retrieval process on the diffraction image.

To obtain image of the atomic structure, we need to make the electron beam spot size on the sample as small as 10 nm to 100 nm (for example, using 2000 pixels CCD, at 1 Angstrom De Broglie wavelength of electron for 150 eV, the spot size should be 100 nm or smaller). One way to achieve this is to use the electron beam of SEM for LEED analysis. The SEM generally uses high quality electron beams suitable for this purpose. However, the SEM electron gun and its column are fairly large; they do not fit within a hole on the grid and the detector of the conventional configuration of LEED.

CITATION LIST

Non Patent Literature

NPL 1: Zangwill, A., "Physics at Surfaces", Cambridge University Press (1988), p. 33

SUMMARY OF INVENTION

Technical Problem

The conventional structure, in particular, the detection part of the LEED device is too large to be inserted to a typical equipment port of commercially available SEMs. The capability of conducting LEED analysis in the same chamber as SEM would provide scientists with a valuable tool for analyzing delicate surface conditions of specimens without breaking vacuum.

Accordingly, the present invention is directed to a LEED detection module that is compact and effective and that can be inserted into an appropriately designed equipment port or flange of SEM and to a SEM with LEED analysis capability.

An object of the present invention is to provide a LEED detection module that is compact and effective and that can be inserted into an appropriately designed or standard equipment port or axially flange of SEM.

Solution to Problem

To achieve these and other advantages and in accordance with the purpose of the present invention, as embodied and broadly described, in one aspect, the present invention provides a low energy electron diffraction (LEED) detection module, including: a first vacuum chamber having an aperture at one end for receiving diffracted electrons from a specimen that is irradiated with a probe beam of electrons; a second vacuum chamber connected to the first vacuum chamber at one end thereof to receive the diffracted electrons that have been transported through the first vacuum chamber, a dimension of the second vacuum chamber in a direction perpendicular to a travelling direction of the diffracted electrons being larger than a corresponding dimension of the first vacuum chamber; a two-dimensional electron detector disposed in the second vacuum chamber at an end opposite to said one end of the second vacuum chamber to which the first chamber is connected, to detect the diffracted electrons; a potential shield made of electrically conductive material disposed generally along an inner surface of the first vacuum chamber and an inner surface of the second vacuum chamber, the potential shield being configured to be applied with a first acceleration voltage to accelerate and focus the diffracted electrons from the specimen; a magnetic lens disposed adjacent to a place where the first vacuum chamber is connected to the second vacuum chamber to expand a beam of the diffracted electrons that have been transported through the first vacuum chamber towards the two-dimensional electron detector; and a generally plane-shaped energy filter to repel electrons having an energy lower than the probe beam of electrons that impinges on the specimen, the energy filter being disposed to have a gap with respect to the potential shield and being configured to be applied with a second acceleration voltage to collimate the beam of the diffracted electrons expanded by the magnetic lens.

In another aspect, the present invention provides a scanning electron microscope (SEM) with low energy electron diffraction (LEED) detection capability, including: the LEED detection module as set forth above; a SEM chamber to house a specimen stage for holding the specimen, the SEM chamber having an open flange to which the LEED detection module is inserted; and a SEM electron gun to emit the probe beam of electrons suitable for SEM analysis towards the specimen, wherein the specimen stage is rotatable to assume a fixed position so that an incident angle of the probe beam relative to a surface of the specimen and an angle at which the first vacuum chamber of the LEED detection module is oriented with respect to the surface of the specimen can be made equal.

Advantageous Effects of Invention

According to one or more aspects of the present invention, it becomes possible to attach the LEED detection module in an axially flange on SEM. Because of this, the LEED module is retractable and detachable. Thus, it becomes possible to perform LEED analysis on the sample under test with SEM and/or with other instrumentations, such as XRF (X-ray fluorescence analysis), to determine contents. In the SEM, because the probe beam typically has size of a few nanometers in diameter, LEED analysis of nano-size areas becomes possible. When inserted into SEM, this instrument will provide very powerful instrumentation technique for surface science, nano-technology and catalysis study.

Additional or separate features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

It is to be understood that both the foregoing general description and the following detailed description are exemplary and explanatory, and are intended to provide further explanation of the invention as claimed.

DESCRIPTION OF EMBODIMENTS

Figure 1:
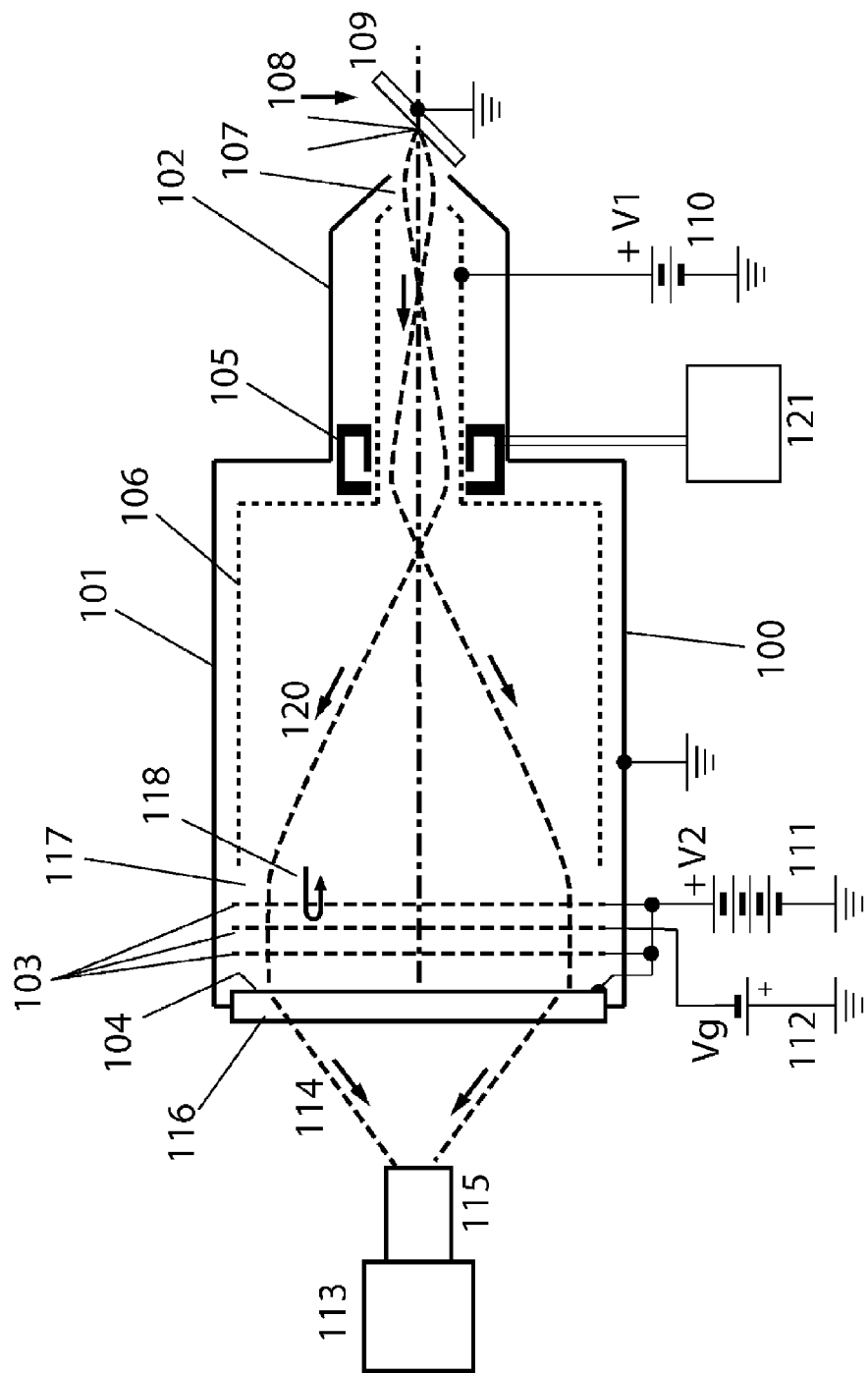
FIG. 1 is a schematic cross-sectional view of a LEED detection module according to an embodiment of the present invention.

FIG. 1 is a schematic cross-sectional view of a LEED detection module 100 according to an embodiment of the present invention. As shown in FIG. 1, the LEED module 100 has a drift tube 102 (a first smaller vacuum chamber) and a vacuum envelope 101 (a second larger vacuum chamber) connected to the drift tube. The drift tube 102 and the vacuum envelope 101 may respectively take generally cylindrical shapes, and may be made of material, such as high quality steel, suited for maintaining appropriate vacuum level therein. A probe beam of electrons 108 emitted from an electron gun in a SEM apparatus is reflected and scattered by the specimen 109, which is mounted on the specimen table in the SEM chamber, and the reflected and scattered electrons (diffracted electrons) are directed to an aperture of the drift tube 102. Here, to have symmetric arrangement, the specimen 109 is depicted as tilted so that the incident angle of the probe beam relative to the surface of the specimen and an angle at which the drift tube 102 is oriented with respect to the specimen surface are equal.

A potential shield 106 is provided as shown in the figure, and is applied with acceleration voltage V1. The potential shield 106 can be made of any appropriate electrically conductive material, such as metal. An energy filter (screen grids) is provided at the end of the vacuum envelope to act as an energy filter to repel inelastic electrons. In this embodiment, the energy filter 103 is constituted of three grids each made of conductive material, such as metal. The two outer grids are applied with acceleration voltage V2 (111). The middle grid is applied with the bias voltage Vg (112). Magnetic lens (focusing lens) 105 focuses the electrons and guides them into the vacuum envelope 101 with the aide of voltage differential developed by the potential shield 106 and the energy filter 103. The magnetic lens 105 is powered by power supply 121.

Figure 2:
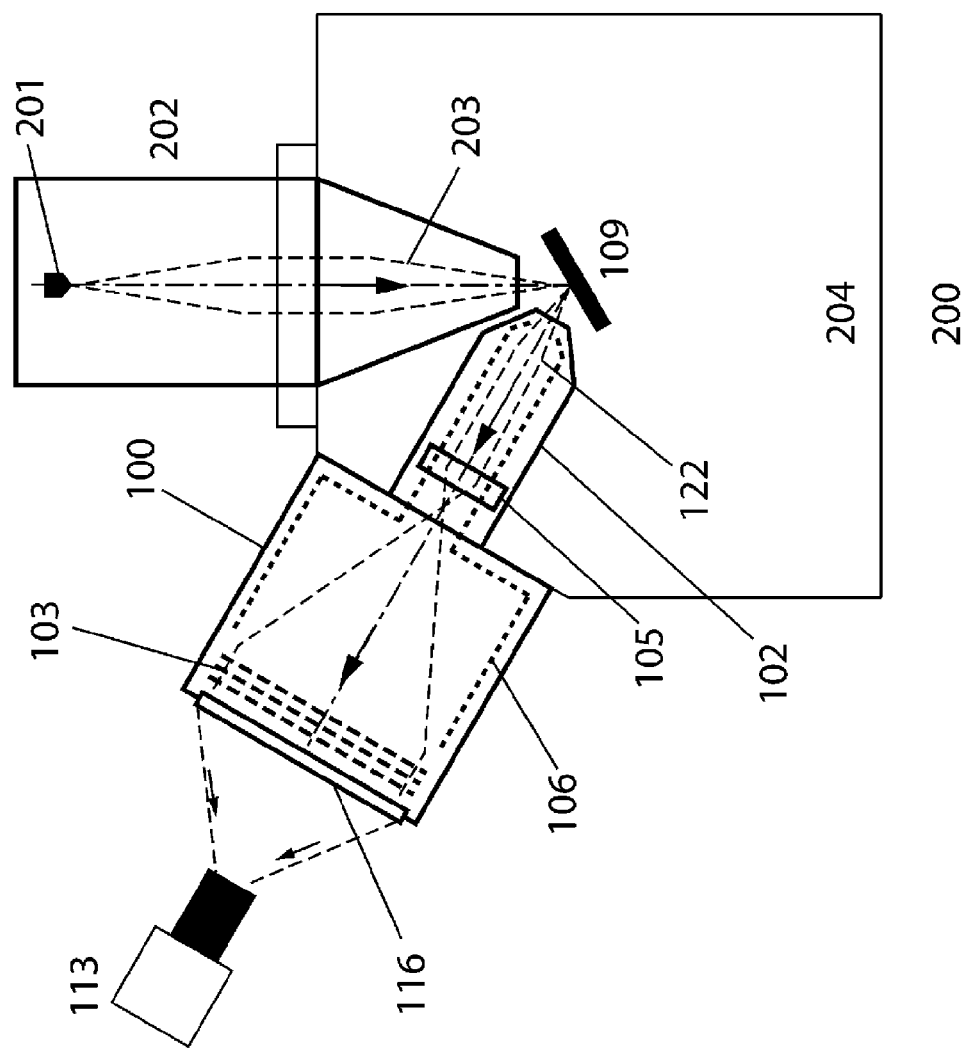
FIG. 2 is a schematic cross-sectional view of a SEM equipped with the LEED detection module of FIG. 1 in which the LEED detection module 100 is inserted into a service open flange of the SEM at 30 degrees to detect reflected and diffracted electrons.

FIG. 2 is a schematic cross-sectional view of a SEM equipped with the LEED detection module of FIG. 1 in which the LEED detection module 100 is inserted into a service open flange of the SEM that is angled at 30 degrees to detect reflected and diffracted electrons, as an example. As shown in FIG. 2, SEM 200 has vacuum chamber 204 and is provided with SEM column 202 having electron gun 201 therein. The probe electron beam (depicted as 203 in FIG. 2) is directed to specimen 109 to generate scattered electrons 122. In this example, the specimen is tilted so that the incident angle and the reflection angle of electrons are the same. Most of currently available commercial SEM has this 30 degree service flange.

When observing an LEED pattern, the scan motion of electron beam is stopped (the SEM mode is stopped), and the position of the beam spot is fixed at a desired location. Prior to this LEED mode, the sample surface can be investigated with the SEM mode. For the LEED analysis, an electron beam at the energy of 50 to 500 eV and with the spot size of 1 nm to 100 nm in diameter, for example, may be used.

Scattered electrons from the sample surface enter the aperture of drift tube 102, and are accelerated by the electro-static accelerating field generated at the gap 107 formed with the potential shield 106 to which the positive potential V1 (110) is applied (FIG. 1). For example, scattered electrons within an opening angle of 60 to 80 degrees in total will be accelerated. There is focusing effect associated with the electrostatic acceleration, which will focus the electron beam toward the axis of the drift tube. If desired, additional magnetic focus lenses (solenoid coils with yoke) may be provided to aid beam transport through a beam pipe having, for example, 10 mm in diameter.

The last magnetic lens 105 acts as a beam expander to match the beam size with a detection area of a two-dimensional electron detector. As the two-dimensional electron detector, a CCD direct electron detector, phosphor with a CCD or CMOS camera may be used, for example. If desired, an MCP (micro-channel plate) may be additionally provided to increase the number of electrons in front of the detector, which enhances the sensitivity. With the use of such additional device, it is estimated that the probe beam current may be reduced to, for example, 1 pA. Generally, a lower beam current is important to reduce sample damages on biological specimens.

In order to eliminate inelastic components (electrons with lower energy than the incident probe beam directed to the specimen), this embodiment employs energy filter 103 constituted of three screen grids to apply a negative bias that is slightly lower than the initial beam energy, thereby reflecting lower energy electrons 118 back. In more detail, as shown in FIG. 1, a positive voltage V2 (111), which is higher than the voltage V1 at the potential shield 106, is applied to the first and third grids and to the 2D electron detector (which is phosphor coating 104 with $TiO_2$ conducting layer on glass window 116 in this embodiment). With this configuration, due to the electrostatic acceleration at the second gap 117, the electron trajectory before reaching the grids becomes parallel to the axis, which lowers energy filtering errors due to residual transverse electron velocity.

For example, V1=+2 kV is applied to the potential shield 106, V2=+4 kV is applied to the first and third screen grids 103 and to the detector (phosphor coating with $TiO_2$ conductor layer 104), and Vg=−290 V is applied to the second grid (in the case of 300 eV electron beam).

In this embodiment, as shown in FIGS. 1 and 2, CCD camera 113 with optical lens 115 may be used behind the glass window 116 coated with phosphor to capture two-dimensional image (intensity distribution of electrons) by receiving light 114 from the glass window 116 to perform LEED analysis. Other CCD or CMOS detector having a large detection area may be used instead.

With the above-described configuration, because the probe beam 108 has a sufficiently small spot, specimen surfaces within small area-as small as a few nm-may be studied. Combining this feature with traditional SEM mode operation, this LEED detection module provides powerful instrumentation for surface science and also related industries (semiconductor, solar cell, Li-ion battery and biology).

Further, because of at least some of the features of the LEED detection module 100 explained above, the LEED detection module 100 may be made compact and can be constructed to fit within a typical or standard open flange found in many SEM or similar apparatus. This is made possible by introducing an electro-static acceleration gap 107 close to the collision point of the incoming electron beam on the specimen. With this configuration, the diffracted electrons are accelerated, and at the same time are focused with the electro-static focusing action associated with the electric acceleration in the gap 107. Because of this, the drift tube 102 can be constructed to be a small size/diameter.

The diffracted electrons that are transported along the drift tube 102 of small diameter are then transported to outside chamber. Using focusing magnetic lens 105, the diffracted beam of electrons 120 is strongly focused and expanded to match its size with the energy filter 103 and the size of the detector (glass window with phosphor 116). By means of the second acceleration gap 117 between the end of the potential shield 106 and the screen grids 103, the electrons are accelerated, and at the same time are collimated. By properly determining the acceleration voltages V1 and V2, and the initial voltage Vb of the probe beam 108, the trajectory of the diffracted electrons can be made in parallel; hence substantially flat plane-shaped screen grids 103 can be used.

Flat screen grids are much easier to fabricate than concave grids, which have been used in conventional LEED device. LIGA (Lithographie, Galvanoformung, Abformung: Lithography, Electroplating, and Molding) processes can be employed to make metal screen grids 103 with fine pitch. For example, a 50-micrometer pitch honeycombed grid with fine ribs of thickness less than 10 micrometers can be made using a 50-micrometer thick metal sheet. Using such fine grids, high resolution imaging becomes possible.

Figure 3:
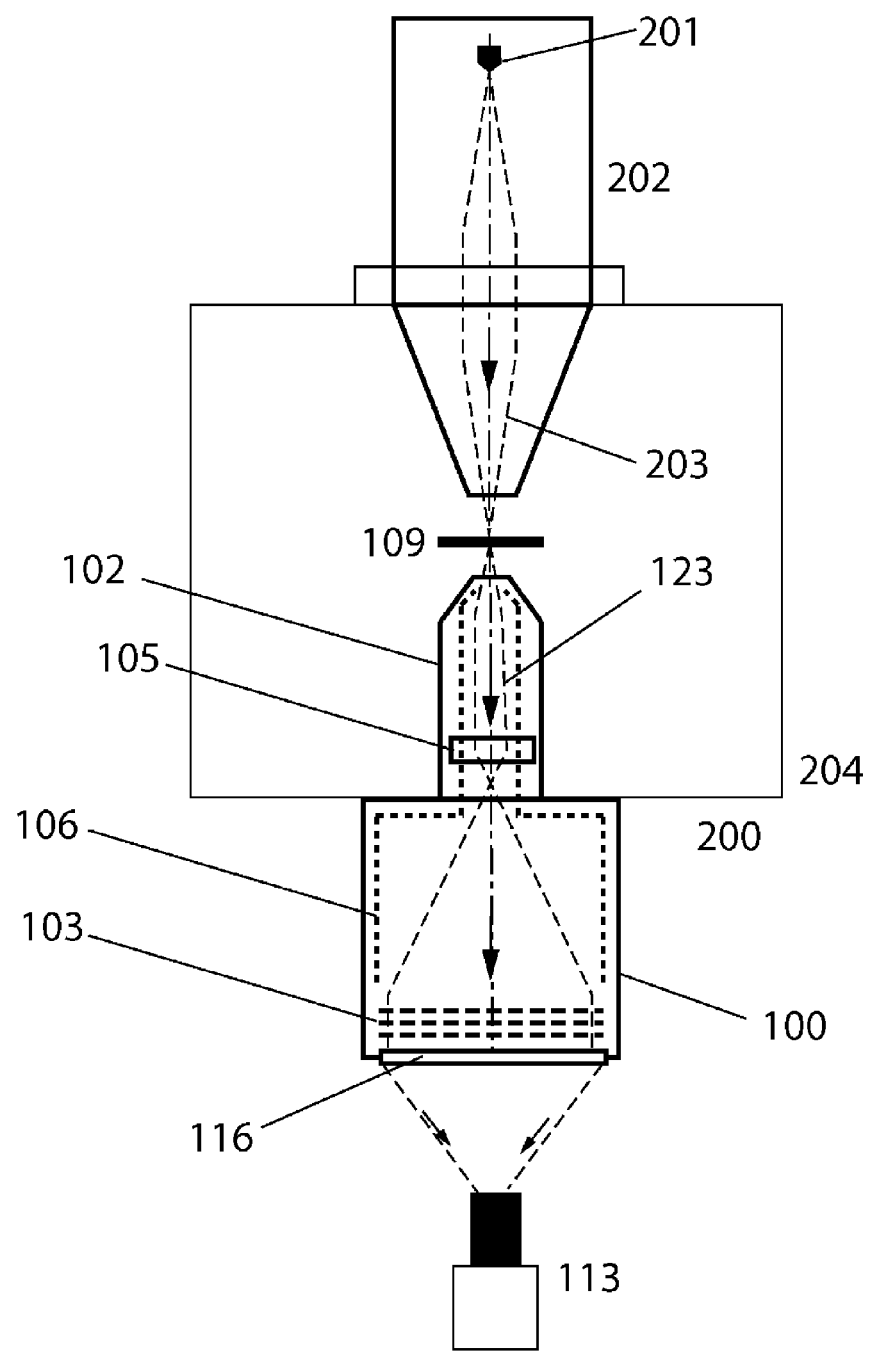
FIG. 3 is a schematic cross-sectional view of a SEM equipped with the LEED detection module of FIG. 1 where the LEED detection module is inserted into a service open flange behind the sample so that the LEED detection module and the SEM column are arranged in a straight line so as to detect transmitted and diffracted electrons.

FIG. 3 is a schematic cross-sectional view of a SEM equipped with the LEED detection module of FIG. 1 where the LEED detection module is inserted into a service open flange behind the sample so that the LEED detection module and the SEM column are arranged in a straight line to detect transmitted and diffracted electrons (scattered electrons 123). This arrangement makes it possible to detect diffraction in the same manner as TEM (transmission electron microscope). Uniqueness in this exemplary configuration of the present invention is that TEM analysis can be conducted with very low energy, for example, at 100 eV where conventional TEM does not work. Today, extremely thin layer samples are available, such as graphene, or GO (graphene oxide), and BN (boron nitride). Low energy electron diffraction study of transmission type is becoming increasingly important.

It will be apparent to those skilled in the art that various modification and variations can be made in the present invention without departing from the spirit or scope of the invention. Thus, it is intended that the present invention cover modifications and variations that come within the scope of the appended claims and their equivalents. In particular, it is explicitly contemplated that any part or whole of any two or more of the embodiments and their modifications described above can be combined and regarded within the scope of the present invention.

REFERENCE SIGNS LIST

100 LEED Detection Module
101 Vacuum Envelope
102 Drift Tube
103 Energy Filter (Screen Grids)
104 Phosphor Coating with $TiO_2$ Conducting Layer
105 Magnetic Lens (Focusing Lens)
106 Potential Shield
107 First Electro-Static Acceleration Gap
108 Probe Beam
109 Specimen
110 Acceleration Voltage $V_1$
111 Acceleration Voltage $V_2$
112 Energy Filter Bias
113 CCD Camera
114 Light
115 Optical Lens
116 Glass Window with Phosphor
117 Second Acceleration Gap
118 Low Energy Electrons
120 Electron
121 Power Supply for Magnetic Lens
122 Scattered Electrons
123 Scattered Electrons
200 Scanning Electron Microscope
201 Electron Gun
202 SEM Column
203 Electron Beam
204 Vacuum Chamber

The invention claimed is:

1. A low energy electron diffraction (LEED) detection module, comprising:
   a first vacuum chamber having an aperture at one end for receiving diffracted electrons from a specimen that is irradiated with a probe beam of electrons;
   a second vacuum chamber connected to the first vacuum chamber at one end thereof to receive the diffracted electrons that have been transported through the first vacuum chamber, a dimension of the second vacuum chamber in a direction perpendicular to a travelling direction of the diffracted electrons being larger than a corresponding dimension of the first vacuum chamber;
   a two-dimensional electron detector disposed in the second vacuum chamber at an end opposite to said one end of the second vacuum chamber to which the first chamber is connected, to detect the diffracted electrons;
   a potential shield made of electrically conductive material disposed generally along an inner surface of the first vacuum chamber and an inner surface of the second vacuum chamber, the potential shield being configured to be applied with a first acceleration voltage to accelerate and focus the diffracted electrons from the specimen;
   a magnetic lens disposed adjacent to a place where the first vacuum chamber is connected to the second vacuum chamber to expand a beam of the diffracted electrons that have been transported through the first vacuum chamber towards the two-dimensional electron detector; and
   a generally plane-shaped energy filter to repel electrons having an energy lower than the probe beam of electrons that impinges on the specimen, the energy filter being disposed to have a gap with respect to the potential shield and being configured to be applied with a second acceleration voltage to collimate the beam of the diffracted electrons expanded by the magnetic lens.

2. The LEED detection module according to claim 1, wherein the energy filter comprises a plurality of screen grids disposed in parallel with each other and perpendicularly to the travelling direction of the diffracted electrons.

3. The LEED detection module according to claim 1, wherein the two-dimensional electron detector comprises a glass window coated with phosphor and a conductive layer.

4. The LEED detection module according to claim 1, wherein the energy filter comprises three screen grids disposed parallel to each other and perpendicularly to a travelling direction of the diffracted electrons, and
   wherein among said three screen grids, a first grid closest to the first vacuum chamber and a third grid that is farthest are configured to be applied with the second acceleration voltage, and a middle grid is configured to be applied with a bias voltage.

5. The LEED detection module according to claim 4, wherein the two-dimensional electron detector comprises a glass window coated with phosphor to be reacted with the diffracted electrons, and a conductive layer, the conductive layer being configured to be applied with the second acceleration voltage.

6. The LEED detection module according to claim 5, further comprising a camera to capture an image generated by the phosphor coated on the glass window that receives the diffracted electrons.

7. The LEED detection module according to claim 6, wherein the camera is a CCD camera.

8. The LEED detection module according to claim 1, wherein the two-dimensional electron detector includes one of a CCD camera, a CMOS camera, and a CCD electron direct detector.

9. The LEED detection module according to claim 1, further comprising an additional magnetic lens in the first vacuum chamber to focus or collimate the beam of the diffracted electrons travelling in the first vacuum chamber.

10. The LEED detection module according to claim 1, wherein the first and second vacuum chamber are both generally cylindrical shape, and a diameter of the second vacuum chamber is larger than a diameter of the first vacuum chamber.

11. The LEED detection module according to claim 1, further comprising a micro-channel plate in front of the two-dimensional electron detector to increase a sensitivity.

12. A scanning electron microscope (SEM) with low energy electron diffraction (LEED) detection capability, comprising:
   the LEED detection module as set forth in claim 1;
   a SEM chamber to house a specimen stage for holding the specimen, the SEM chamber having an open flange to which the LEED detection module of claim 1 is inserted; and
   a SEM electron gun to emit the probe beam of electrons suitable for SEM analysis towards the specimen,
   wherein the specimen stage is rotatable to assume a fixed position so that an incident angle of the probe beam relative to a surface of the specimen and an angle at which the first vacuum chamber of the LEED detection module is oriented with respect to the surface of the specimen can be made equal.

* * * * *